United States Patent [19]

Ranger

[11] Patent Number: 5,492,831
[45] Date of Patent: Feb. 20, 1996

[54] SHARED PERIPHERAL ANALYTICAL SYSTEM

[75] Inventor: Craig B. Ranger, Glendale, Wis.

[73] Assignee: Lachat Instruments, Milwaukee, Wis.

[21] Appl. No.: 340,151

[22] Filed: Nov. 15, 1994

[51] Int. Cl.⁶ .................................................. G01N 35/00
[52] U.S. Cl. .......................... 436/50; 436/149; 436/161; 436/179; 436/807; 422/62; 422/82.01; 422/89; 422/116
[58] Field of Search ............................ 422/62–67, 82.01, 422/89, 116; 435/809; 436/63, 43, 50, 53, 149, 179, 158, 161, 807, 808, 174

[56] References Cited

U.S. PATENT DOCUMENTS

| | | | |
|---|---|---|---|
| 4,158,545 | 6/1979 | Yamashita et al. | 436/47 |
| 4,166,095 | 8/1979 | Kling et al. | 422/67 |
| 4,366,119 | 12/1982 | Takeuchi | 422/65 |
| 4,459,265 | 7/1984 | Berglund | 422/64 |
| 4,483,927 | 11/1984 | Takekawa | 436/43 |
| 4,678,752 | 7/1987 | Thorne et al. | 435/291 |
| 4,953,075 | 8/1990 | Nau et al. | 364/140 |
| 5,046,018 | 9/1991 | Flewelling et al. | 364/497 |
| 5,055,260 | 10/1991 | Roberge et al. | 436/158 |
| 5,104,621 | 4/1992 | Pfost et al. | 422/67 |
| 5,108,703 | 4/1992 | Pfost et al. | 422/65 |
| 5,108,928 | 4/1992 | Menard et al. | 436/53 |
| 5,358,691 | 10/1994 | Clark et al. | 422/67 |

OTHER PUBLICATIONS

Chem., Biomed., and Environ, Instrumentation, 10(4), 353–370 (1980).
Alternatives for Laboratory Automation—Research/Development (May, 1977) 40–54.
American Laboratory, vol. 8, No. 9 (Sep. 1976) 71–83.

*Primary Examiner*—Michael G. Wityshyn
*Assistant Examiner*—Rachel Heather Freed
*Attorney, Agent, or Firm*—Foley & Lardner

[57] ABSTRACT

A system for performing chemical analyses includes at least two analyzers and at least one peripheral device capable of serving either analyzer. A control system is coupled to the analyzers and to the peripheral device and selectively commands the peripheral device to serve one or the other of the analyzers depending upon the analyses requested for each analyzer and the analytical method applied. A control system providing sharing of peripheral devices in such a system is also provided, as is a method for performing chemical analyses wherein a peripheral device is shared by analyzers. The system permits simultaneous and asynchronous analysis for a variety of analytes while reducing the physical space occupied by the system and the idle time of both the analyzers and the peripheral devices.

14 Claims, 4 Drawing Sheets

SHARED PERIPHERAL ANALYTICAL SYSTEM

FIELD OF THE INVENTION

The present invention relates generally to an apparatus and a method for performing chemical analyses. More particularly, the invention relates to performing chemical analyses using at least two analysis instruments and at least one peripheral device capable of serving either instrument, wherein a control system commands and coordinates sharing of the peripheral device by the samples and flexible scheduling of various analytical tests and methods.

BACKGROUND OF THE INVENTION

A number of applications exist for chemical analysis techniques for detecting the presence and concentration of known analytes in test samples. Such applications include testing and monitoring of foodstuffs, beverages, feeds, soils, plants and water supplies for pollutants or controlled substances. The analysis process typically involves collection and preparation of chemical samples, analysis of the samples in an analytical instrument and recording of the results of the analysis. A number of steps may be involved in the preparation of each sample, including dilution, addition of reagents and transport of the sample to the analytical instrument. Depending upon the type of analysis to be performed and the analyte to be detected or measured, various instruments may be employed. Moreover, various test methods may be used for certain analytes involving parallel operations in multiple instruments.

Automation of chemical analysis equipment has permitted sophisticated analyses to be performed at greatly increased speed without sacrificing the quality of analytical results. Such automation typically involves arranging a number of peripheral devices, such as samplers, diluters, injection valves, pumps and other sample preparation apparatus to serve an analyzer where test samples are analyzed for the presence and concentration of various analytes. Some known systems include a central computer system or other signal processing unit for coordinating the operation of the various components and for storing and tabulating test results. Such systems are described, for example, in U.S. Pat. Nos. 4,158,545, 4,166,095, 4,366,119, 4,459,265 and 4,483,927.

In known automated analysis systems test samples are typically arranged in sample cups. In certain known systems a series of such cups is advanced along a path where the sample is prepared for analysis, such as by adding appropriate reagents. The series of cups eventually reaches an analysis station including an analyzer, such as a spectrophotometric instrument, where the sample is analyzed. In other known systems, sample cups are arranged in an array and samples are aspirated by a transport system and delivered to an analytical instrument. In either case, results of the analyses may be collected and recorded in a central processing unit for later printout or display.

While such systems represent a considerable improvement over manual analysis techniques, they are not without drawbacks. For example, known automated chemical analysis systems typically associate a number of peripheral devices with a single analyzer. Such systems may approach continuous usage of the analyzer by coordinating preparation and delivery of subsequent test samples by the peripheral devices during the time a previous sample is being analyzed. However, where the time required for sample preparation and delivery is much less than the time required for analysis, the benefit achieved by such systems is ultimately diminished as the peripheral devices become idle.

A further drawback of known automated chemical analysis systems is the space required for the associated analyzers and peripheral devices. Because each analyzer is typically served by dedicated peripheral devices, the space required for the overall system is multiplied where several analyzers are present, each with its associated peripheral devices. This problem is particularly acute when analyzers and peripheral devices are incorporated in a mobile analytical laboratory for performing on-site analytical operations, such as for environmental pollutants. Such mobile laboratories are often housed in a specially equipped vehicle in which benchspace is especially limited. A particular need presently exists for improved automated chemical analysis systems for on-site compliance monitoring of U.S. Environmental Protection Agency standards, such as by flow injection analysis (FIA) and ion chromatography (IC), Such applications require complex analytical systems capable of performing analyses quickly and reliably, but that occupy a minimum of benchspace. Moreover, such systems should be capable of testing for a range of analytes through various methods, some of which call for parallel analyses to be performed in different types of analyzers (e.g. FIA and IC). Finally, they should be capable of facilitating scheduling of such tests and recording test results as they are available for display and printout.

SUMMARY OF THE INVENTION

The present invention features a novel approach to automated chemical analysis wherein peripheral devices capable of serving at least two analyzers are effectively shared by the analyzers, reducing the number of peripheral devices required in the overall system and thereby the benchspace occupied by the system. Coordination of this peripheral sharing affords maximum utilization of both the analytical instruments and the peripheral devices. Thus, in accordance with one aspect of the invention, an apparatus for performing chemical analyses comprises a first and a second analyzer configured to perform chemical analyses. The apparatus further includes at least one peripheral device and a control circuit coupled to the analyzers and to the peripheral device. The peripheral device is configured to selectively perform pre-analysis operations in a predetermined sequence for the analyzers in response to control signals. The control circuit is configured to generate control signals and to apply the control signals to the peripheral device for commanding the peripheral device to selectively perform the pre-analysis operations for the analyzers.

In addition to the novel chemical analysis apparatus, the present invention also features a control system for an analytical system. The control system is designed for application on a system including first and second analyzers for performing chemical analyses on test samples and at least one peripheral device responsive to control signals. The control system includes a memory circuit and a control circuit. The memory circuit is configured for storing a predetermined sequence of analytical operations to be performed on each test sample. The control circuit is coupled to the first and second analyzers, to the peripheral device and to the memory circuit and is configured to generate control signals and to apply the control signals to the peripheral device to selectively command the peripheral device to perform pre-analysis operations for the first and second analyzer to execute the sequence of analytical operations.

Another important aspect of the present invention is a novel method for performing chemical analyses in an analytical system. The method is designed to be applied in a system including a first and a second chemical analyzers and a peripheral device configured to perform pre-analysis operations in response to commands from a control circuit. The system also includes a control circuit coupled to the peripheral device and to the analyzers. The method includes the steps of commanding the peripheral device to perform a pre-analysis operation for the first chemical analyzer and performing a first analysis operation in the first analyzer. The peripheral device is then commanded to perform a pre-analysis operation for the second analyzer and a second chemical analysis operation is performed in the second analyzer. In a preferred embodiment, the second analyzer is polled to determine if it requires use of the peripheral device. If so, the peripheral device is commanded to serve the second analyzer and once the service of the second analyzer is complete, the peripheral device may be commanded to serve the first or a different analyzer.

Other features of the invention and other ways in which the present invention provides the features will become apparent to one skilled in the art after reading the following detailed description of a particularly preferred embodiment.

BRIEF DESCRIPTION OF THE DRAWINGS

The present invention will become more fully understood from the following detailed description, taken in conjunction with the accompanying drawings, wherein like reference numerals refer to like parts, in which.

DESCRIPTION OF THE PREFERRED EMBODIMENT

Before proceeding to the detailed description of the preferred embodiment of the present invention, several comments would be appropriate with regard to the applicability and scope thereof.

First, while the analytical instruments included in the system described may generally be of any type, the system is particularly suited to FIA and IC instruments. Other preferred instruments include a continuous flow analyzer (CFA), such as a segmented flow analyzer (SFA), an elemental analyzer or an immunoassay analyzer. It has been found that the combination of FIA and IC instruments permits a wide range of tests for common analytes. These instruments are typically used individually or in combination depending upon the analytes to be detected and the analytical method employed for detecting the analytes. An analytical "method" comprises a predetermined sequence of sample preparation and analysis steps required to detect and measure analytes of interest. For example, a method for detecting and measuring pollutants in drinking water may call for analysis by an FIA instrument (producing a single "peak" representing a voltage signal proportional to the concentration of a particular analyte, such as nitrate) and an IC instrument (producing a series of "peaks" indicating the presence of various identifiable analytes). Because the times required to perform such tests are different for different analyzers, is has been found that the efficiency in utilizing both the analyzers and peripheral devices can be greatly improved by permitting sharing of the peripheral devices among the analyzers.

For example, when a particular analytical method calls for analysis by both FIA and IC instruments, the present system schedules peripheral devices to perform pre-analysis operations, such as preparing and delivering samples, for both instruments so that the instruments may perform simultaneous and asynchronous analyses, that is, separate tests running in parallel but beginning at different times. Once available, the results of the tests are stored and tabulated by the system controller. When other methods call for analysis by only one instrument, the present system permits scheduling of other, separate analyses to be performed simultaneously and asynchronously on other instruments with peripheral devices again being shared by the instruments.

The present system may accommodate commercially available FIA instruments having a single channel or multiple channels. The presently preferred embodiment is designed to accommodate up to four analyzers and up to eight total channels. Such instruments typically include injection valves associated with each channel, each valve having two states, "load" and "inject". Electrical control signals to the injection valves actuate the valves to shift from one state to the other, such as to a closed state to commence an analysis on a loaded sample (i.e. inject a sample) or to an open state for receiving a subsequent sample for analysis (i.e. load a sample). In addition, these instruments typically include various types of analytical detectors, one such detector being associated with each channel of the instrument. The particular detectors installed in an instrument will generally depend upon the analytes to be detected and the manner in which they are to be measured. Such detectors include fluoride electrodes, pH electrodes, fluorimeters, flame photometers and conductivity detectors. Other detectors can include absorbance and inverse absorbance detectors adapted to produce a voltage signal proportional or inversely proportional to absorbance. For the purposes of scheduling and control in the present system, injection valves and detectors are generally not considered shared peripheral devices, but are dedicated to the associated instrument.

Similarly, IC instruments supported by the system may be unsuppressed or chemically suppressed for eliminating background noise caused by the process eluant. Commercially available instruments of this type typically include one injection valve of the type described above and one channel. Such instruments generally produce a number of "peaks" corresponding to various analytes. As with FIA instruments, the injection valve of an IC instrument is not considered a shared peripheral device for the purposes of the present system. In addition, each IC instrument may be served by a dedicated high pressure or low pressure pump for eluant and reagent delivery.

With regard to the control system for the scheduling and commanding of the various components of the system, the presently preferred platform is a personal computer system based on an Intel 386 or equivalent microprocessor, or a more advanced model (e.g. Intel 486 or equivalent microprocessor), capable of multi-tasking. The control system may include a graphical user interface, such as a screen display with menus of user-selectable options to facilitate programming and monitoring of tests and methods. However, other platforms and interfaces may be envisioned that permit control of peripheral and analytical devices as described below without necessarily affording the same facility in programming and monitoring.

Finally, the shared peripheral devices of the present system are generally considered those devices designed to perform pre-analysis operations for the analyzers as opposed to post-analysis peripherals such as data storage devices, printers and the like. Such pre-analysis operations typically include sampling, diluting, addition of reagents, washing (e.g. of probes used for sample collection) and transport and delivery of samples to analyzers. However, this list is not intended to be exhaustive and, depending upon the particular types of analysis to be performed by the system, other operations and peripherals could be included and shared in the manner described below.

Figure 1:
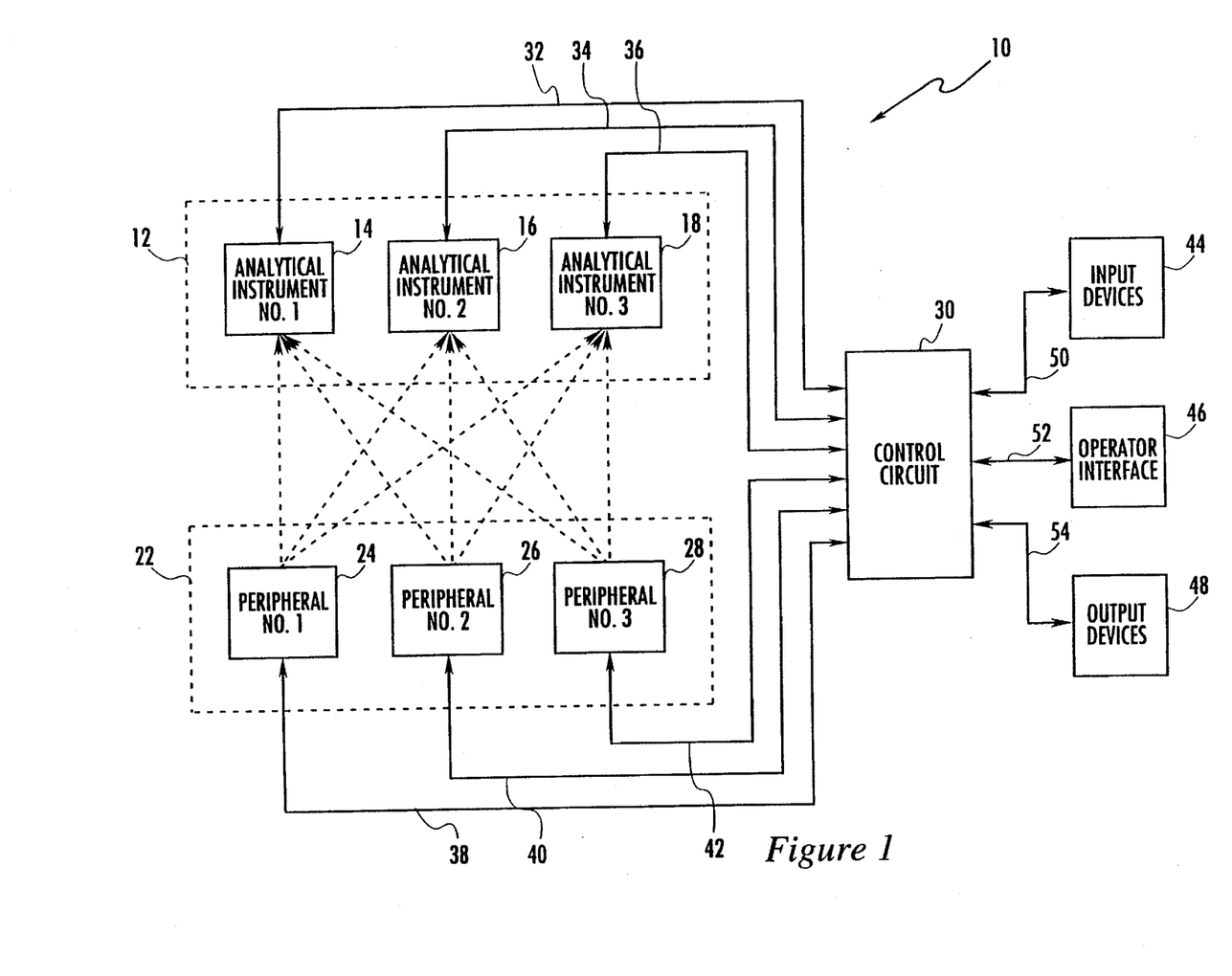
FIG. 1 is a schematic block diagram of a shared peripheral analytical system in accordance with an embodiment of the present invention illustrating the typical functional and informational relationships among the various components.

Proceeding now to a description of the components comprising the preferred embodiment of the present invention, attention should first be directed to FIG. 1. An automated chemical analysis system is illustrated in a schematic block diagram and designated generally by the reference numeral 10. System 10 includes a group of analyzers 12 including first, second and third analyzers 14, 16 and 18, and a group of peripheral devices 22 including first, second and third peripheral devices 24, 26 and 28. System 10 further includes a control circuit 30 coupled to analyzers 14, 16 and 18 and to peripheral devices 24, 26 and 28 via data buses 32, 34, 36, 38, 40 and 42 respectively. Data buses 32, 34, 36, 38, 40 and 42 may be commercially available serial or parallel buses as required for the particular analyzer or peripheral device, such as a standard RS232 bus.

While three analytical instruments are illustrated in FIG. 1, system 10 may include as few as two such instruments. In a presently preferred embodiment, system 10 includes one multichannel FIA instrument 14, such as the QuikChem 8000-A analyzer available from Lachat Instruments of Milwaukee, Wis., and one suppressed IC instrument 16, such as the QuikChem 8000-B analyzer available from Lachat Instruments.

Similarly, in its most simple form system 10 may include a single peripheral device 24 shared by the analyzers. When a single peripheral device 24 is provided in system 10, this device will typically be a sampler, such as the XYZ sampler available from Lachat Instruments. Such commercially available samplers, generally referred to as "autosamplers", include a tray for one or more sample racks, a probe for aspirating samples and a Cartesian robot for supporting and moving the probe. Samples, such as liquid samples of products to be analyzed, are placed in open containers or cups arranged within each rack at identifiable locations or addresses. Such racks may also include calibration and quality control samples of known composition used to calibrate and verify the accuracy of the analytical instruments. The probe is coupled to a vacuum and pressure source, such as a peristaltic pump, that can be selectively actuated for aspirating samples into the probe from the sample containers and discharging the sample from the probe into the injection valve of an analytical instrument. The robot typically includes stepper motors coupled to lead screws or similar transmission components supporting the sample probe. The stepper motors rotate a desired amount in response to pulsed electrical signals to move the probe between desired addresses where test samples are located for analysis and known locations of other peripheral devices (such as a diluter 26 or reagent delivery system 28) and analyzers 14, 16, 18. Thus, such samplers are configured to collect and deliver samples in response to appropriate control signals depending upon the pre-analysis operations to be performed.

Other shared peripheral devices may include a diluter, such as the Dual Resolution Diluter available from Lachat Instruments, and a peristaltic pump, such as the Reagent Pump available from Lachat Instruments, for implementing a continuous flow reagent delivery system.

Peripheral devices 24, 26, 28 are configured to selectively serve (i.e. perform pre-analysis operations for) each analytical instrument 14, 16, 18, as indicated by the dashed arrows from peripheral devices 24, 26, 28 to instruments 14, 16 and 18 in FIG. 1. For example, peripheral device 24, such as an autosampler, may collect and deliver test or calibration samples to one channel of FIA instrument 14 and subsequently collect and deliver a different or the same sample to IC instrument 16. While the analyses of those samples are in progress, autosampler 24 may collect and deliver a third sample to a diluter, then collect the diluted sample for delivery to a second channel of FIA instrument 14. If IC instrument 16 terminates its scheduled analysis before FIA instrument 14, autosampler 24 may be commanded to prepare and deliver the next scheduled sample to IC instrument 16. Analytical instruments 14, 16, 18 thus share, or are served by, peripheral devices 24, 26, 28, eliminating the need for separate dedicated peripheral devices for each instrument and increasing the efficiency of the overall system by permitting the peripheral devices to serve one analyzer while another analyzer is in operation.

Buses 32 through 42, coupling analyzers 14, 16, 18 and peripheral devices 24, 26, 28 to control circuit 30, serve a dual role. First, they provide a communications link from control circuit 30 to the associated device through which control signals may be applied to the device for commanding a desired action, such as opening or closing an injection valve in an analyzer, or aspirating, transporting or delivering samples, reagents or diluting liquids by a peripheral device. For example, in the case of analyzers 14, 16, 18, control circuit 30 will apply signals commanding the injection valve associated with the instrument to close for sample injection and analysis or to open for sample loading. Similarly, in the presently preferred embodiment, autosampler 24 and diluter 26 are shared by FIA and IC instruments 14, 16 and are coupled to COM ports of control circuit 30. In operation, autosampler 24 typically contains unknown (test) samples, calibration and quality control samples arranged at addressable locations, while diluter 26 serves to dilute samples through a sequence of sample aspiration and diluent dispensing. Both autosampler 24 and diluter 26 receive commands in the form of an ASCII set via their respective data links with control circuit 30.

Secondly, buses 32 through 42 provide a data link between the associated analyzer or peripheral device and control circuit 30 for data transmission. Such data typically relates to the results of analyses performed in analyzers 14, 16, 18, but may include signals from peripheral devices, including feedback signals indicating that a desired action has or has not been accomplished. For example, as indicated above, autosampler 24 and diluter 26 receive instructions via their respective buses 38 and 40. In response to these instructions, these peripheral devices attempt the action commanded and generate return codes indicating success or error, also in the form of an ASCII set, and apply these signals to control circuit 30 via buses 38 and 40.

Control circuit 30 is also coupled to one or more input devices 44, an operator interface 46 and one or more output devices 48 via buses 50, 52 and 54. Input devices 44 preferably include a computer keyboard and mouse (coupled to control circuit 30 by separate parallel or serial connectors). However, a specialized keyboard or other device may be provided, particularly where other computer platforms are used. Operator interface 46 preferably includes a screen display with icon and window-based status displays, as will be discussed more fully below with reference to FIG. 3. Finally, output devices 48 preferably include a printer for producing tabulated data output and graphical charts representing the results of analyses.

Figure 2:
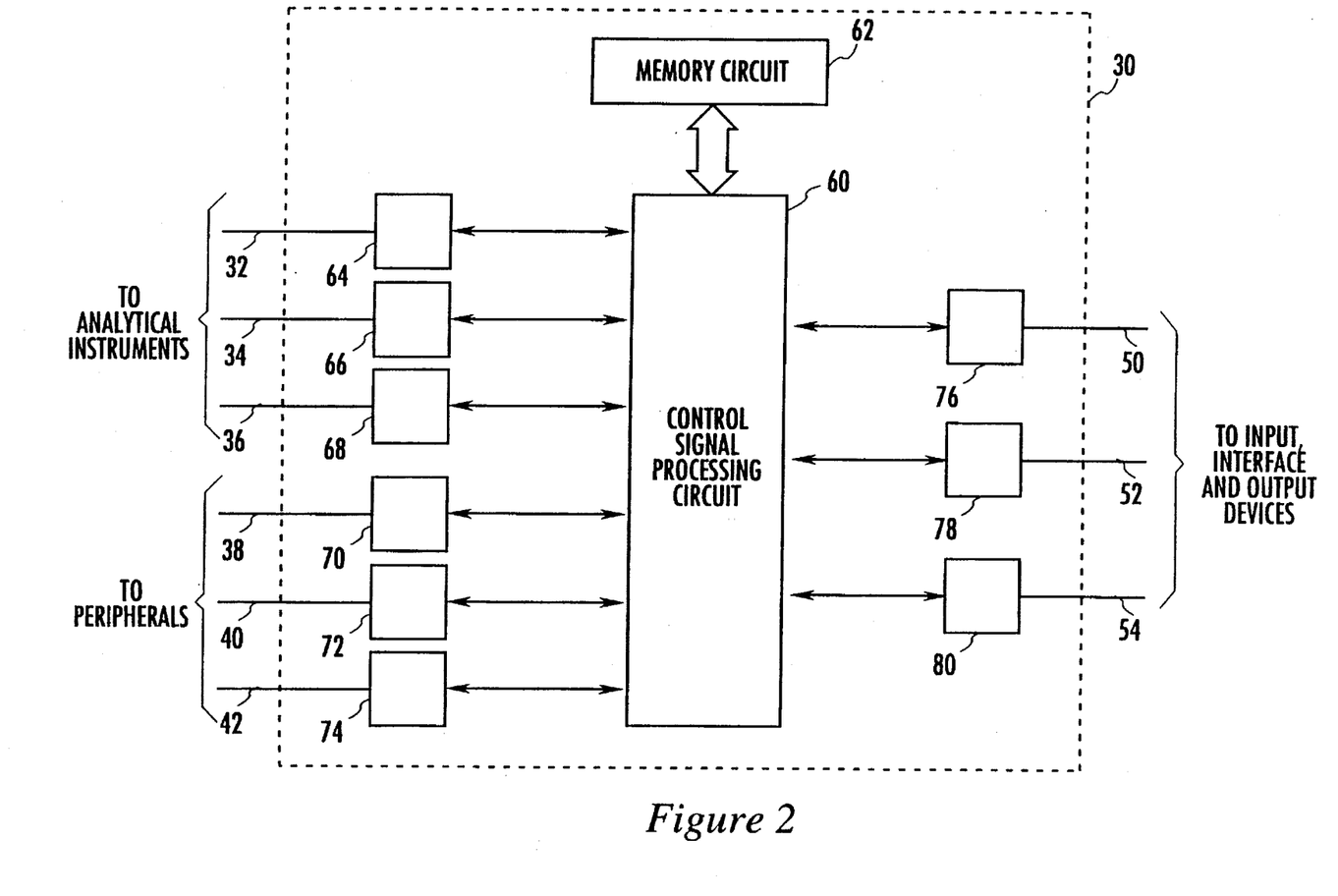
FIG. 2 is a block diagram of a typical control circuit for implementing the system depicting the internal circuits configured to permit interactive scheduling of analytical tests and sharing of peripheral devices among instruments.

As illustrated in FIG. 2, control circuit 30 includes a central digital signal processing unit 60 and a memory circuit 62 in communication with signal processing circuit 60. Memory circuit 62 typically includes one or more disc drives and solid state memory media having read only memory (ROM) for storing the general system configuration (i.e. the operating system and application program) and random access memory (RAM) for temporarily storing data relating to current commands, test results, instrument status and the like. Signal processing circuit 60 is also linked to interface circuits 64, 66 and 68 for sending instructions to and receiving data from analytical instruments 14, 16 and 18, and to interface circuits 70, 72 and 74 for communicating with peripheral devices 24, 26 and 28. Control circuit 30 also includes interface circuits 76, 78 and 80 for communication between signal processing circuit 60 and input and output devices 44 and 48, and operator interface 46. Circuits 64 through 80 will typically include appropriate signal conditioning circuits and drivers for the associated devices, and may be configured in part or entirely by standard operating system software designed to configure I/O and COM ports in a personal computer system. Moreover, signal processing circuit 60, memory circuit 62 and interface circuits 64 through 80 are preferably included in an appropriately configured (programmed) computer. While FIG. 2 schematically illustrates data flow, a standard bus, such as an ISA bus, is the preferred embodiment of coupling circuits 64 through 80 to digital signal processing circuit 60.

Memory circuit 62 preferably includes a predetermined base set of commands, such as for actuating injection valves of analyzers 14, 16, 18 and commanding movement of peripheral devices 24, 26, 28. Moreover, memory circuit 62 preferably also includes preset routines consisting of chains of such commands most frequently required for performing analyses for common analytes in accordance with established analytical methods. In operation, these preset commands and methods, relating to specific analytes to be detected in specific samples using one or more of the analytical instruments, are selected by an operator and communicated to control circuit 30 via input devices 44, such as by selecting options from a computer screen display menu. Thus, standard methods may be requested and other, customized methods may be generated by the operator when required. For example, a method for detecting the presence of ammonia in samples of waste water may call for analysis by an FIA instrument, whereas a method for detecting the presence of several anions such as fluoride, chloride, nitrite, nitrate, phosphate and sulfate may call for analysis by an IC instrument. Once the address of the samples and the method of analysis are selected, signal processing circuit 60 identifies the appropriate sequence of commands for peripheral devices 24, 26, 28 and analytical instruments 14, 16, 18 to perform the requested analysis based upon routines stored in memory circuit 62.

As successive tests on other samples are requested by the operator, signal processing circuit 60 establishes a queue of the requested tests and schedules utilization of the analytical instruments and peripheral devices accordingly. While this scheduling may follow the order in which the various analysis requests enter the queue, it advantageously includes logic for prioritizing scheduled analyses, such as based upon estimations of the processing times for the various tests, thereby permitting the peripheral devices to perform tasks based upon the anticipated time when the analyzer, or channels of the analyzer, will become available for a subsequent analysis operation. Such information is also preferably included in the routines stored in memory circuit 62. As specific tasks are reached in the queue, signal processing circuit 60 generates control signals for accomplishing the tasks and applies these signals to the appropriate peripheral devices and analyzers via their associated buses. As return signals are received by signal processing circuit 60 indicating the assigned tasks have been performed, control circuit 30 advances to the next scheduled analysis operation. Signals representative of the results of analyses are applied to signal processing circuit 60, are converted to standardized values and enter the appropriate data files for storage in memory circuit 62, display on interface.46 and output on output devices 48.

In the presently preferred system, for example, peripheral devices 24, 26, 28 are scheduled to serve (i.e. perform pre-analysis operations for) FIA instrument 14 in accordance with methods selected by an operator in the order in which they are selected (i.e. first-in, first-out). However, IC instrument 16 has a generally higher priority for sharing peripheral devices 24, 26, 28 due to the relatively long time required for IC analyses as compared to FIA analyses. Therefore, control circuit 60 commands peripheral devices 24, 26, 28 to serve FIA instrument 14, but cycles through a control routine in which IC instrument 16 is polled to determine if it is available to receive a subsequent sample for a scheduled IC method. If so, control circuit 60 temporarily interrupts service of FIA instrument 14 once the then-current service is complete and commands peripheral 24, 26, 28, or certain of these as required by the IC method, to perform operations for IC instrument 16. Once these operations are complete, peripheral devices 24, 26, 28 may be commanded to resume service of FIA instrument 14. As will be apparent to those skilled in the art, similar prioritizing schemes may be implemented depending upon such factors as the number and types of analyzers included in the system, the number and types of peripheral devices included, the anticipated times required for performing certain analyses or preparing certain samples or operator-imposed interrupts or priorities.

Figure 3:
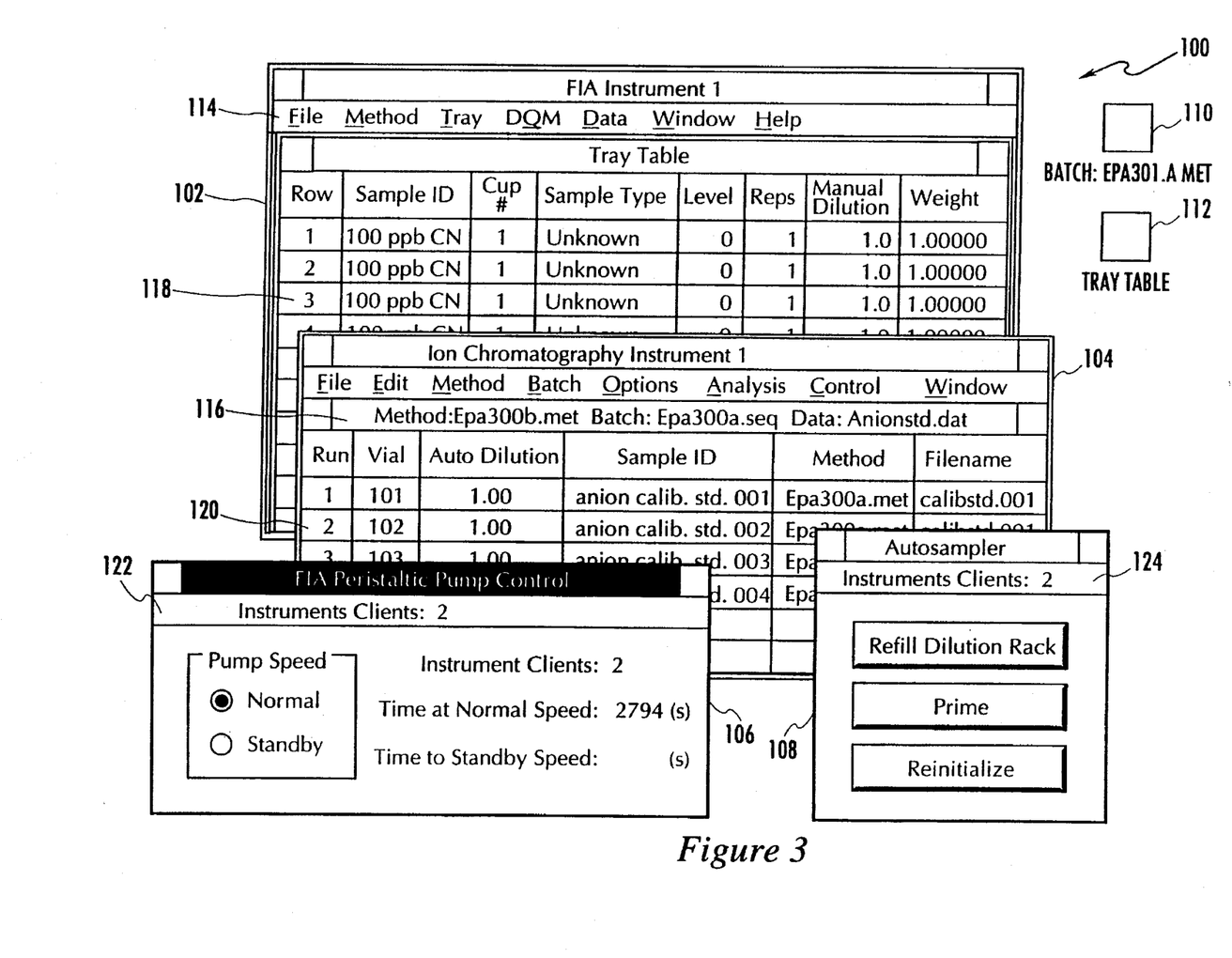
FIG. 3 is a representation of a computer screen display illustrating scheduling of simultaneous and asynchronous analytical testing and sharing of peripheral devices among analytical instruments performing the testing, in this case two analyzers or "clients"

In the preferred embodiment, control and monitoring of analytical instruments 14, 16, 18 and peripheral devices 24, 26, 28 are managed through a computer screen display 100, as illustrated in FIG. 3. Display 100 is produced on interface device 46, such as a computer screen, and provides a graphical interface including instrument control and status windows 102, 104 and peripheral control and status windows 106, 108. During the time when analyses are being performed or the information available in the windows is not immediately required, the windows may be closed or collapsed, as represented by icons 110 and 112 such as by clicking a mouse or other input device 44 while a screen pointer overlays a particular region of display 100.

Each instrument control and status window 102, 104 includes a menu-driven options bar 114, 116 and a data display area 118, 120. Option bars 114 permit selection of the desired analytical method, identification and addressing of test samples and any special instructions such as dilution, reagent addition, scaling and the like that may differ from pre-programmed method routines stored in memory circuit 62. Scheduled analyses appear in data display areas 118, 120, along with results of the analyses once received from the analyzers.

Each peripheral control and status window 106, 108 includes a bar 122, 124 indicating the number of "clients" or analyzers currently sharing the peripheral device. For example, in FIG. 3, status bar 124 in window 108 shows that autosampler 24 is currently performing operations for two analyzers. Similarly, status bar 122 in window 106 shows that another peripheral device, an FIA peristaltic pump, is also currently being shared by two analyzers. Windows 106 and 108 may also include menus or control options available to a user for performing specific functions upon request, such as by clicking a mouse with a screen pointer within a particular screen area. For example, as illustrated in FIG. 3, autosampler 24 may be commanded to refill a dilution rack by clicking in a corresponding area in window 108, or the speed of a peristaltic pump may be selected by an operator by clicking in a corresponding area in window 106.

EXAMPLE

Figure 4:
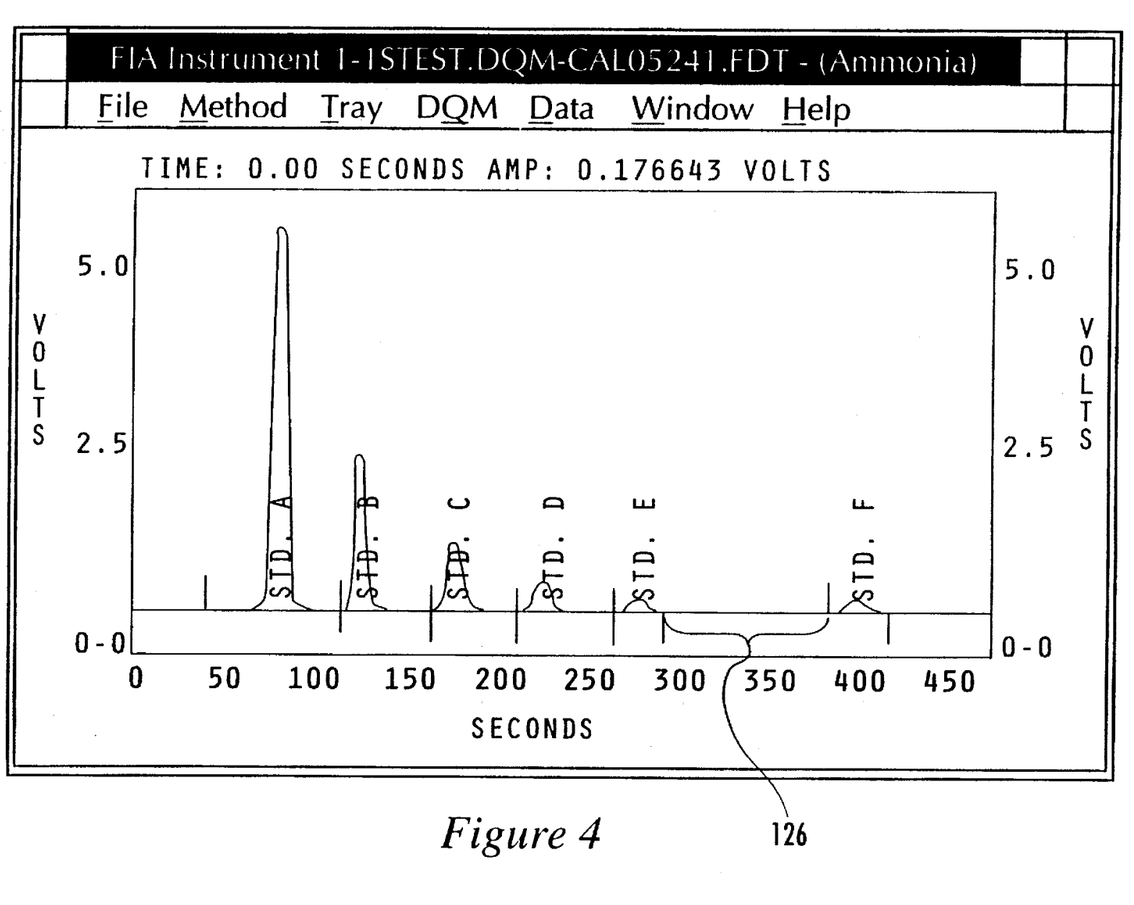
FIG. 4 is a graphical representation of results of chemical analyses performed on an FIA instrument illustrating an example of how the invention can command the sharing of peripheral devices between different instruments.

With reference to FIG. 4, the following provides an example of how system 10 can be used to perform simultaneous and asynchronous analyses through sharing of peripheral devices. In this example, system 10 includes a multi-channel FIA instrument 14 (the QuikChem 8000-A analyzer from Lachat Instruments), an IC instrument 16 (the QuikChem 8000-B analyzer from Lachat Instruments), an autosampler 24 with racks for test samples, calibration samples and quality control samples and including a continuously circulating wash bath (the XYZ sampler from Lachat Instruments), a diluter 26 (the Dual Resolution Diluter from Lachat Instruments) and a continuous flow reagent injection system including a peristaltic pump (the Reagent Pump from Lachat Instruments). Control and monitoring functions are provided via a personal computer 30 with an Intel 486 microprocessor serving as the controller. A number of pre-programmed analyte detection methods are stored in the memory 62 of the computer, including methods for detecting ammonia, nitrates, nitrites, phosphates and sulfates, among others. Thus, for example, system 10 is capable of utilizing different methods simultaneously on different channels of FIA instrument 14, such as for detecting concentrations of ammonia and phosphate, while applying a third method for detection of a number of analytes in IC instrument 16 through a serial or separations technique.

In the example, FIA instrument 14 is scheduled to process an ammonia calibration sample through an FIA method in which six "Standards", A through F, are measured, and IC instrument 16 is scheduled to analyze drinking water samples. FIA instrument 14 is scheduled to be served first. In accordance with the selected method, controller 30 instructs autosampler 24 to go to the address containing the calibration sample. Once at the location, autosampler 24 is commanded to lower the sample collection probe and aspirate an appropriate volume of the sample. As each assigned task is completed, autosampler 24 applies feedback signals to controller 30 informing it of success and controller 30 proceeds to the next scheduled routine command. With the sample thus collected, autosampler 24 is instructed to transport the sample to FIA analyzer 14 and to pump the sample from the probe into the FIA injection valve. Once the sample is delivered, the FIA injection valve is commanded to close, thus loading the sample into the analyzer for testing. Autoampler 24 is next commanded to proceed with loading the subsequent sample for the FIA method. The peaks labeled Standards A through E in FIG. 4 reflect the results of the first five FIA analyses performed in this way.

While Standard E is being acquired for analysis in FIA instrument 14, IC instrument 16 demands autosampler 24. In response to this demand, autosampler 24 completes aspirating and delivering Standard E as previously scheduled and is commanded to proceed to the wash bath for the time required for the subsequent IC method. Autosampler 24 is then commanded to collect a drinking water sample from the address programmed in the IC schedule and to deliver the sample to IC instrument 16. Once this sample is loaded into the instrument, the injection valve is closed and the IC analysis begins. Autosampler 24 then resumes service of FIA instrument 14. The brief interruption in the FIA method caused by the IC service is reflected in the additional delay in the baseline of the FIA results, designated by the reference numeral 126 in FIG. 4, between the Standard E peak and the Standard F peak (approximately 100 seconds more than the delay would have been without interruption).

While the invention is adapable via various modifications and alternative forms, specific embodiments have been shown and described by way of example only. It should be understood that the invention is not intended to be limited to the particular forms disclosed. Rather, the invention is to cover all modifications, equivalents and alternatives falling within the spirit and scope of the invention as defined by the appended claims.

I claim:

1. An apparatus for performing chemical analyses comprising:

a first and a second analyzer configured to perform chemical analyses, the analyses performed by the first analyzer being shorter in duration than the analyses performed by the second analyzer;

a peripheral device configured to selectively perform pre-analysis operations on a plurality of test samples for the first and second analyzers in response to control signals; and a control circuit coupled to the first and second analyzers and to the peripheral device, the control circuit being configured to schedule analysis of a plurality of test samples on the first analyzer and to schedule analysis of at least one test sample on the second analyzer, the control circuit being further configured to generate control signals and to apply the control signals to the peripheral device for commanding the peripheral device to selectively perform said pre-analysis operations for the first analyzer on the plurality of test samples scheduled for the first analyzer and to interrupt service of the first analyzer by said peripheral device after completion of a then current pre-analysis operation being performed on one of the plurality of test samples scheduled for the first analyzer but prior to completion of pre-analysis operations on remaining test samples scheduled for the first analyzer to perform a pre-analysis operation on the at least one test sample scheduled for the second analyzer based on availability of the second analyzer to perform its scheduled analysis.

2. An apparatus as set forth in claim 1 wherein the first analyzer is capable of performing a first type of chemical analysis and the second analyzer is capable of performing a different type of chemical analysis.

3. An apparatus as set forth in claim 1 wherein the first analyzer is a flow injection analyzer and the second analyzer is a ion chromatography analyzer.

4. An apparatus as set forth in claim 1 wherein the peripheral device is chosen from a group of devices consisting of a sampler, a pump and a diluter.

5. The apparatus as set forth in claim 1 further comprising a memory circuit configured to store a plurality of predetermined, operator selectable command routines for performing analyses by the analyzers and pre-analysis operations by the peripheral device.

6. In an analytical system including first and second analyzers for performing chemical analyses on a plurality of test samples and a peripheral device responsive to control signals to perform pre-analysis operations on the test samples, the analyses performed by the first analyzer being shorter in duration than the analyses performed by the second analyzer, a control system comprising:

a memory circuit configured to store a predetermined sequence of analytical operations to be performed on each test sample; and a control circuit coupled to the first and second analyzers, the peripheral device and the memory circuit, the control circuit being configured to schedule analysis of a plurality of test samples on the first analyzer and to schedule analysis of at least one test sample on the second analyzer, the control circuit being further configured to generate control signals to execute the predetermined sequence of analytical operations by applying the control signals to the peripheral device to selectively command the peripheral device to perform said pre-analysis operations for the first analyzer on the plurality of test samples scheduled for the first analyzer and to interrupt performance of said pre-analysis operations for the first analyzer by the peripheral device after completion of a then current pre-analysis operation being performed on one of the plurality of test samples scheduled for the first analyzer but prior to completion of the pre-analysis operations on remaining test samples scheduled for the first analyzer and perform a pre-analysis operation on the at least one test sample scheduled for the second analyzer based on availability of the second analyzer to perform its scheduled analysis.

7. The control system as set forth in claim 6 further comprising an operator interface coupled to the control circuit for inputting the analytical operations to be performed by each analyzer.

8. The control system as set forth in claim 6 further comprising a second memory circuit coupled to the control circuit and configured to receive and store data representative of the results of chemical analyses performed by the analyzers.

9. The control system as set forth in claim 6 further comprising an operator interface coupled to the control circuit for displaying the status of the analyzers and peripheral device.

10. A method for performing chemical analyses in an analytical system including a first chemical analyzer for performing chemical analyses on a plurality of test samples, a second chemical analyzer for performing chemical analysis on at least one test sample, a peripheral device configured to perform pre-analysis operations in response to commands from a control circuit and a control circuit coupled to the peripheral device and to the analyzers, the control circuit being configured to schedule said chemical analyses of the plurality of test samples by the first analyzer and to schedule said chemical analysis of the at least one test sample by the second analyzer, the analyses performed by the first analyzer being shorter in duration than the analyses performed by the second analyzer, the method comprising the steps of:

(a) commanding the peripheral device to perform a pre-analysis operation on one of the test samples scheduled for the first chemical analyzer;

(b) performing a first chemical analysis operation in the first analyzer on the sample on which the pre-analysis operation has been performed;

(c) repeating steps (a) and (b) while cyclically polling the second chemical analyzer to determine when the second chemical analyzer is available to perform a chemical analysis on the scheduled test sample for the second analyzer;

(d) based on availability of the second chemical analyzer to perform a chemical analysis on the test sample scheduled for the second chemical analyzer, completing step (a) and then commanding the peripheral device to perform a pre-analysis operation on the test sample scheduled for the second analyzer; and (e) performing a second chemical analysis operation in the second analyzer.

11. The method set forth in claim 10 wherein the chemical analysis operation performed in step (b) is different from the chemical analysis operation performed in step (e).

12. The method set forth in claim 10 wherein the first chemical analyzer is a flow injection analyzer and the second chemical analyzer is an ion chromatography analyzer.

13. The method set forth in claim 10 wherein the peripheral device is chosen from a group of devices consisting of a sampler, a pump and a diluter.

14. The method set forth in claim 10 wherein the chemical analysis operation of step (b) is performed at least partially simultaneously with the chemical analysis operation of step (e).

* * * * *